United States Patent [19]

Foerster et al.

[11] Patent Number: 5,980,874
[45] Date of Patent: Nov. 9, 1999

[54] TRANSLUCENT ANTIPERSPIRANTS/ DEODORANTS

[75] Inventors: Thomas Foerster, Erkrath; Marcus Claas, Hilden; Bernhard Banowski, Duesseldorf, all of Germany

[73] Assignee: Henkel Kommanditgesellschaft auf Aktien, Duesseldorf, Germany

[21] Appl. No.: 09/011,925

[22] PCT Filed: Aug. 9, 1996

[86] PCT No.: PCT/EP96/03520

§ 371 Date: Mar. 19, 1998

§ 102(e) Date: Mar. 19, 1998

[87] PCT Pub. No.: WO97/06776

PCT Pub. Date: Feb. 27, 1997

[30] Foreign Application Priority Data

Aug. 17, 1995 [DE] Germany .......................... 195 30 220

[51] Int. Cl.$^6$ ................................ A61K 7/32; A61K 7/00
[52] U.S. Cl. ................................ 424/65; 424/66; 424/67; 424/68; 424/400; 424/401
[58] Field of Search ................... 424/65, 66, 67, 424/68, 400, 401

[56] References Cited

U.S. PATENT DOCUMENTS 3,547,828 12/1970 Mansfield et al. .
5,138,046 8/1992 Wuesr et al. ...................... 536/18.6

FOREIGN PATENT DOCUMENTS

| 19 43 689 | 3/1970 | Germany . |
| 38 27 534 | 2/1990 | Germany . |
| 43 37 041 | 5/1995 | Germany . |
| WO93/07249 | 4/1993 | WIPO . |

OTHER PUBLICATIONS

*Emulsions: Theory and Practice* 182–86 (1965).

J. Jpn. Oil Chem. Soc. (Yukagaku) 44(2):116–20 (1995) (Chem. Abstracts 122:191041j (1995)).

J. Pharm. Pharmacol. 27:385–96 (1975) (plus abstract).

*Primary Examiner*—Shelley A. Dodson
*Attorney, Agent, or Firm*—Ernest G. Szoke; Wayne C. Jaeschke; Glenn E. J. Murphy

[57] ABSTRACT

The invention relates to translucent antiperspirants based on finely-divided, sprayable microemulsions. The invention also relates to microemulsion concentrates and a method for the production of antiperspirants from such concentrates. The stable microemulsions according to the invention thereby have a droplet diameter of substantially less than 100 nm.

23 Claims, No Drawings

TRANSLUCENT ANTIPERSPIRANTS/ DEODORANTS

BACKGROUND OF THE INVENTION

Field of the Invention

This invention relates to translucent antiperspirants/ deodorants based on fine-droplet sprayable microemulsions. The invention also relates to microemulsion concentrates and to a process for the production of translucent antiperspirants/deodorants from such concentrates. The stable microemulsions according to the invention essentially have a droplet diameter of less than 100 nm.

DESCRIPTION OF THE INVENTION

Prior Art

The use of oil-in-water emulsions as carriers for cosmetic and dermatological active substances has been known for some time. One difficulty is that the stability of the carrier system is often adversely affected by the nature of the active substances. It was already known from German patent application P 43 37 041.1 that very fine-droplet emulsions produced by the phase inversion process are particularly suitable as carriers for organic deodorants, perfume oils and sun protection factors. However, it could not be concluded from this document that such emulsions would also be suitable as carriers for water-soluble, inorganic, astringent antiperspiration agents.

The problem addressed by the invention was to improve the skin and mucous membrane compatibility of antiperspirants by using an emulsion of which the oil components have a softening and inflammation-inhibiting effect on the skin as carriers for the astringent agents. The particularly high compatibility would be achieved by using a fine-droplet emulsion as carrier for the antiperspiration agent. The problem with such fine-particle emulsions was above all that the usual oil-in-water emulsions were not sufficiently stable in the presence of the inorganic agents and that the viscosity of the microemulsions generally increased so drastically with decreasing droplet size that the microemulsions could no longer be processed in the form of a sprayable carrier.

It has now surprisingly been found that the problem stated above can be solved by using as the carrier a very fine-droplet emulsion such as can be obtained, for example, by using large quantities of suitable nonionic surfactants, optionally in conjunction with co-emulsifiers. The invention provides both translucent, fine-droplet and also low-viscosity and hence sprayable antiperspirants.

Substances acting as antiperspirants generally have a deodorizing effect as well so that, in the context of the present invention, antiperspirants also include compositions where for the most part the deodorizing effect is predominant. This can be the case, for example, with compositions which contain the antiperspiration agent in such low concentrations that the deodorizing component of the action spectrum predominates over the antiperspiration component. Accordingly, the term antiperspirants as used in the following is synonymous with antiperspirants/deodorants or antiperspirants and deodorants.

Accordingly, the present invention relates to translucent antiperspirants in the form of a sprayable, fine-droplet oil-in-water emulsion containing
a) 0.5 to 30% by weight of a water-immiscible oil phase,
b) 40 to 90% by weight of water and, based on 1 part by weight of oil phase,
c) 0.35 to 30 parts by weight of nonionic emulsifiers, more particularly from the group of alkyl polyglycosides,
d) optionally 0.1 to 7.5 parts by weight of a lipophilic co-emulsifier and other typical additives,
characterized in that the emulsion additionally contains 0.1 to 25% by weight of an inorganic astringent antiperspiration agent and in that the droplet size of the emulsified phase is essentially between 10 and 100 nm.

The antiperspirant formulations according to the invention are distinguished by particularly high dermatological compatibility of the antiperspiration agent which they retain even in the event of regular use.

Suitable water-soluble, inorganic astringent antiperspiration agents are, above all, salts of aluminium, zirconium or zinc.

Examples of these suitable antihydrotic agents include aluminium chloride, aluminium chlorohydrate, aluminium dichlorohydrate, aluminium sesquichlorohydrate and complex compounds thereof with 1,2-propylene glycol, aluminium hydroxyallantoinate, aluminium chloride tartrate, aluminium/zirconium trichlorohydrate, aluminium/ zirconium tetrachlorohydrate, aluminium/zirconium pentachlorohydrate and complex compounds thereof with amino acids, for example with glycine.

However, aluminium hydroxychlorides and adducts thereof with water-soluble glycols are particularly suitable. Water-soluble salts are understood to be salts of which at least 1 % by weight dissolve in water at 20° C.

According to the invention, the water-soluble, inorganic astringent antiperspiration agents are used in quantities of 0.1 to 25% by weight. In certain cases, however, it is of advantage to use the water-soluble, inorganic astringent antiperspiration agents in quantities of 1 to 15% by weight, preferably in quantities of 2 to 10% by weight and more preferably in quantities of 4 to 9% by weight. By contrast, certain antiperspirant formulations may also contain 0.1 to 10% by weight or preferably 1 to 6% by weight of the antiperspiration agent whereas formulations, for example in concentrate form, may easily contain quantities of 8 to 25% by weight, preferably 10 to 22% by weight and, more preferably, 10 to 18% by weight of the antiperspiration agent.

Carriers for the antiperspiration agent are so-called microemulsions. Microemulsions are optically isotropic, thermodynamically stable systems which contain a water-insoluble oil component, emulsifiers and water. the clear or rather transparent appearance of the microemulsions is a consequence of the small droplet size of the dispersed emulsion droplets which is essentially below 100 nm and, on average, is always below 50 nm.

Although microemulsions have often been described in the literature, their production involves considerable difficulties because the existence ranges of the microemulsions in the three-phase diagram of oil component, water and emulsifiers are generally very small and the position of these existence ranges is influenced to a very large extent by structural features of all the various components and any other ingredients of such systems.

The methods for producing microemulsions are known in principle. Mixtures of water, oil component and emulsifiers are prepared and the optically isotropic, thermodynamically stable existence ranges in the three-phase diagram formed from these components are determined. Suitable cosmetic oil components, hereinafter referred to as the oil phase, are any water-insoluble, dermatologically compatible oils and fats and mixtures thereof with solid paraffins and waxes. Preferred dermatologically compatible oil components are hydrocarbons which are liquid at 20° C., for example paraffins oils and synthetic hydrocarbons such as, for example, 1,3-di-(2-ethylhexyl)-cyclohexane. Other particularly suitable oil components are di-n-alkyl ethers such as, for example, di-n-octyl ether, di-(2-ethylhexyl)-ether, lauryl methyl ether or octyl butyl ether.

A particularly versatile group of cosmetic oil components is the group of fatty acid and fatty alcohol esters, for example isopropyl myristate, n-butyl stearate, 2-ethylhexyl caprylate, cetyl oleate, glycerol tricaprylate, cocoalcohol-($C_{12-18}$)-caprylate/caprate and others.

Also suitable are naturally occurring ester oils such as, for example, jojoba oil or liquid vegetable triglyceride oils such as, for example, olive oil, sunflower oil, soybean oil, rapeseed oil, almond oil, the liquid fractions of coconut oil or beef tallow and synthetic triglyceride oils. Other suitable cosmetic oil components are dicarboxylic acid esters such as, for example, di-n-butyl adipate, di-n-butyl sebacate, di-(2-ethylhexyl)-adipate, di-(2-hexyldecyl)-succinate and diisotridecyl azelate. Suitable diol esters are, for example, ethylene glycol dioleate, ethylene glycol diisotridecanoate, propylene glycol di-(2-ethylhexanoate), propylene glycol diisostearate, propylene glycol dipelargonate, butanediol diisostearate and neopentyl glycol dicaprylate.

Di-n-alkyl ethers are preferably used as a constituent of the oil phase, di-n-octyl ether being particularly preferred. The di-n-alkyl ethers are present in a quantity of at least 30% by weight, preferably 40% by weight and, more preferably, at least 50% by weight. Particularly advantageous embodiments of the invention contain di-n-alkyl ethers in the oil phase in a quantity of at least 60%. It can be of advantage to increase the percentage ether content to a value of, for example, 80 or 90% by weight. The percentage ether content of the oil phase may even be 100% by weight, in which case the phase width of the microemulsion is particularly large.

The antiperspirants according to the invention may contain the oil phase in a quantity of advantageously 2 to 15% by weight and, preferably, 2 to 10% by weight, based on the total antiperspirant in the emulsion.

The water content in the emulsion of the final antiperspirant is normally between 40 and 90% by weight. In view of the narrow phase widths of the emulsion, the water content generally has to be varied, a water content of 60 to 90% by weight and, more particularly, 70 to 88% by weight having proved to be of advantage for the antiperspirants according to the invention.

The microemulsions normally contain a hydrophilic nonionic emulsifier with an HLB value of preferably 8 to 15 as the emulsifier. The HLB value (hydrophilic/lipophilic balance) can be calculated from the structure of the emulsifier in accordance with the following equation:

$$HLB = \frac{100 - L}{5} \qquad \text{I}$$

where L is the percentage by weight of lipophilic groups, i.e. the fatty alkyl or fatty acyl groups in the emulsifier.

The hydrophilic emulsifiers are, for example, addition products of ethylene oxide with fatty alcohols containing 16 to 22 carbon atoms or with partial esters of polyols containing 3 to 6 carbon atoms and fatty acids containing 14 to 22 carbon atoms. However, addition products of ethylene oxide with fatty acids, with alkyl glycosides, with methyl glycoside fatty acid esters, with fatty acid alkanolamides, with fatty acid-N-alkyl polyhydroxyalkyl amides and other fatty compounds with ethoxylatable substituents are also suitable.

The fatty acid-N-alkyl polyhydroxyalkyl amides are known substances which may normally be obtained by reductive amination of a reducing sugar with ammonia, an alkyl amine or an alkanolamine and subsequent acylation with a fatty acid, a fatty acid alkyl ester or a fatty acid chloride. The fatty acid-N-alkyl polyhydroxyalkyl amides are preferably derived from reducing sugars containing 5 to 6 carbon atoms, more particularly from glucose (fatty acid glucamides).

However, one particularly preferred embodiment of the invention is characterized by the use of alkyl polyglycosides corresponding to the following formula:

in which R is a $C_{8-22}$ alkyl or alkenyl group, Z is a monosaccharide, more particularly glucose, and x stands for its degree of oligomerization, a number of 1.1 to 1.5 and, more particularly, 1.2 to 1.4. The production of such alkyl polyglycosides and their use as surfactants are known, for example, from DE 19 43 689 and from DE 38 27 534. They are produced by reaction of glucose or oligosaccharides with primary alcohols containing 8 to 16 carbon atoms or by transacetalization of starch with, for example, lower alcohols and retransacetalization with a $C_{8-14}$ fatty alcohol.

The nonionic emulsifiers, particularly those from the group of alkyl polyglycosides, are generally used in a quantity of 0.35 to 30 parts by weight per part by weight of oil phase, preferably in a quantity of 0.5 to 10 parts by weight and more preferably in a quantity of 0.6 to 4 parts by weight per part by weight of oil phase. However, particularly advantageous results can be obtained by using the nonionic emulsifiers in a quantity of 0.7 to 1.4 parts by weight per part by weight of oil phase. In this case, it is generally most favorable to use one or more nonionic emulsifiers from the group of alkyl polyglycosides with a chain length of the lipophilic group of 8 to 16 carbon atoms.

It may be necessary to add one or more lipophilic co-emulsifiers to the oil phase in order to obtain the required fine-droplet emulsions. Suitable lipophilic co-emulsifiers are, for example, fatty acid polyol partial esters, fatty alcohols or fatty alcohol polyol ethers.

Fatty acid polyol partial esters in the context of the invention are products of the esterification of fatty acids containing 8 to 22 and preferably 12 to 22 carbon atoms with polyfunctional alcohols having a functionality of 3 to 10, preferably 3 to 6 and more preferably 3 or 4.

Particularly preferred fatty acid polyol partial esters are those in which only one OH function is esterified with a suitable fatty acid. The mixtures formed in such an esterification should advantageously contain 35 to 96% of monoesters, 1 to 50% of diesters and 0.1 to 20% of tri or higher esters.

If glycerol is used as the polyol, the partial esters may be obtained particularly easily by transesterification of natural fats or oils with an excess of glycerol. Suitable natural fats and oils are, for example, beef tallow, lard, palm oil, sunflower oil or soybean oil, preferably natural fats or oils with a particularly high percentage content of oleic acid. Suitable polyols are, for example, propylene glycol, glycerol, erythritol trimethylol propane, pentaerythritol, sorbitol, diglycerol, methyl glycoside or even aldoses such as, for example, glucose or mannose.

Suitable fatty acid polyol partial esters are, for example, the technical glycerol or sorbitan monoesters of myristic acid, palmitic acid, stearic acid and oleic acid or of technical cocofatty acid $C_{12-18}$ cuts. Sorbitan monooleate and stearic acid monoglyceride are preferably used, oleic acid monoglyceride being particularly preferred.

Also suitable are linear and/or branched C8–22 fatty alcohols, which may optionally contain one or more double bonds in the carbon chain, and partial ethers of the polyfunctional alcohols mentioned in the description of the fatty acid polyol partial esters with C8–22 fatty alcohols.

The lipophilic co-emulsifier is optionally used in a quantity of 0.01 to 7.5 parts by weight per part by weight of oil phase, a quantity of 0.1 to 5 parts by weight per part by weight of oil phase being preferred and a quantity of 0.2 to 3 parts by weight per part by weight of oil phase being particularly preferred. In many cases, it can be of advantage to use the lipophilic co-emulsifier in a quantity of 0.2 to 1.4 parts by weight or, preferably, 0.2 to 1.2 parts by weight per part by weight of oil phase.

The ratio of nonionic emulsifier to co-emulsifier should generally be between 1:1 and 20:1 and is preferably between 2:1 and 15:1 or between 2:1 and 10:1. Particularly advantageous results can be obtained where the ratio of nonionic emulsifier to co-emulsifier is between 2.5:1 and 5:1.

In many cases, however, the co-emulsifying effect of the perfume oil optionally used eliminates the need to add co-emulsifiers.

Besides the ingredients discussed thus far, the translucent antiperspirants according to the invention may contain other typical additives, for example water-soluble polyols containing 2 to 8 carbon atoms and 2 to 6 hydroxyl groups. Examples of suitable polyols are ethylene glycol, 1,2-propylene glycol, glycerol, erythritol, trimethylol propane, sorbitol or methyl glycoside. Instead of these polyols, polyethylene glycols or addition products of ethylene oxide with such polyols may also be used.

Lower volatile alcohols should only be present in the antiperspirants according to the invention in very small quantities and preferably not at all. For example, the content of ethanol or isopropanol should not exceed a value of 2% by weight.

However, the antiperspirants according to the invention may additionally contain typical oil-soluble and/or water-soluble auxiliaries in small amounts. Examples of such oil-soluble auxiliaries include inflammation-inhibiting, skin-protecting or pleasantly smelling essential oils, synthetic skin-protecting agents or oil-soluble perfume oils. This group also includes, for example, oil-soluble deodorizing agents such as, for example, triethyl citrate, phenoxyethanol and/or 2,4,4'-trichloro-2'-hydroxydiphenyl ethers which may be added to the emulsion according to the invention, optionally in admixture with oil-soluble preservatives such as, for example, PHB esters.

Typical water-soluble additives are, for example, preservatives, oil- or water-soluble perfumes, pH regulators, for example buffer mixtures, water-soluble thickeners, for example water-soluble natural or synthetic polymers such as, for example, xanthan gum, hydroxyethyl cellulose, polyvinyl pyrrolidone, poly(meth)acrylates or high molecular weight polyethylene oxides.

The present invention also relates to the production of transparent antiperspirants. Their production generally involves a two-stage cold process in which a water-dilutable microemulsion concentrate is initially prepared.

Accordingly, the present invention also relates to translucent microemulsion concentrates containing
a) 20 to 40% by weight of water,
b) 20 to 40% by weight of a water-insoluble oil and, based on 1 part by weight of oil phase,
c) 0.35 to 30 parts by weight of nonionic emulsifiers, more particularly from the group of alkyl polyglycosides, and optionally
d) 0.1 to 10% by weight of perfume oils,
characterized in that the droplet size is essentially between 1 and 100 nm.

The individual constituents correspond to those mentioned above in the description of the antiperspirants according to the invention.

The present invention also relates to a process for the production of translucent microemulsion concentrates which is characterized in that the water-soluble components are dissolved in water while the oil-soluble components are dissolved in the oil phase (optionally at elevated temperature) and the phases are intensively mixed at temperatures of 10 to 90° C. and, more particularly, at temperatures of 20 to 70° C.

If co-emulsifiers which are liquid between 10 and 30° C. are used, they may generally be processed at room temperature, room temperature in the context of the present invention being a temperature in the range from 20 to 25° C. However, an increase in temperature in the production of the microemulsions may be necessary, particularly when a lipophilic wax-like co-emulsifier with a high melting point is used. For example, where glycerol monooleate is used as co-emulsifier, the microemulsion concentrate according to the invention has to be produced by mixing the aqueous phase and the oil phase at a temperature of 65° C. After cooling, a low-viscosity system is obtained into which such additives as, for example, perfume oil may optionally be stirred. A water-clear low-viscosity microemulsion is normally formed and is available as a concentrate in a second process step for producing the translucent antiperspirants according to the invention.

Accordingly, the present invention also relates to a process for the production of translucent antiperspirants, characterized in that a translucent microemulsion concentrate is intensively mixed with an aqueous solution of antiperspiration agents.

The following Examples are intended to illustrate the invention without limiting it in any way.

EXAMPLES

List of the ingredients used:
Plantaren® 1200: $C_{12-16}$ alkyl oligoglycoside (Henkel Corp.)
Plantaren® 2000: $C_{8-16}$ alkyl oligoglycoside (Henkel Corp.)
Examples of formulations for transparent microemulsion concentrates

TABLE 1

Examples of formulations for transparent microemulsion concentrates (in % by weight)

|  | Example 1 | Example 2 |
| --- | --- | --- |
| Plantaren ® 1200 | 11.21 | 0 |
| Plantaren ® 2000 | 7.48 | 26.00 |
| Glycerol monooleate | 4.67 | 0 |
| Dioctyl ether | 26.17 | 20.00 |
| Octyl dodecanol | 6.54 | 0 |
| Triethyl citrate | 0 | 10.00 |
| Perfume oil | 6.54 | 5.0 |
| Water | 37.38 | 39.00 |
| Transmission (650 nm, %) | 99 | 95 |

Examples of formulations for sprayable translucent antiperspirant microemulsions

TABLE 2

Examples of formulations for sprayable translucent antiperspirant microemulsions (final composition in % by weight)

| | Example 3 | Example 4 | Example 5 |
|---|---|---|---|
| Plantaren ® 1200 | 1.71 | 1.71 | 0 |
| Plantaren ® 2000 | 1.14 | 1.39 | 2.40 |
| Glycerol monooleate | 0.71 | 0.71 | 0 |
| Dioctyl ether | 4.00 | 4.00 | 0.09 |
| Octyl dodecanol | 1.00 | 1.00 | 0.02 |
| Perfume oil | 1.00 | 1.00 | 1.00 |
| Aluminium chlorohydrate | 8.00 | 5.00 | 5.00 |
| 1,2-Propylene glycol | 5.00 | 5.00 | 0 |
| Glycerol | 0 | 0 | 5.00 |
| Water | 77.44 | 80.19 | 86.49 |
| Transmission (650 nm, %) | 70.30 | 74.10 | 55.00 |

What is claimed is:

1. A translucent antiperspirant composition in the form of a sprayable, fine-droplet, oil-in-water emulsion, comprising:
   a) 0.5% to 30% by weight of a water-immiscible dermatologically compatible oil phase;
   b) 40% to 90% by weight of water;
   c) 0.35 to 30 parts by weight of a hydrophilic nonionic emulsifier per part by weight of the oil phase; and
   d) 0.1% to 25% by weight of an inorganic astringent antiperspiration agent,
   wherein the size of the droplets is essentially between 10 nm and 100 nm.

2. A composition according to claim 1, further comprising 0.1 to 7.5 parts by weight of a lipophilic co-emulsifier per part by weight of the oil phase.

3. A composition according to claim 1, comprising 2% to 15% by weight of the oil phase.

4. A composition according to claim 3, comprising 2% to 10% by weight of the oil phase.

5. A composition according to claim 1, comprising 60% to 90% by weight of water.

6. A composition according to claim 5, comprising 70% to 88% by weight of water.

7. A composition according to claim 1, comprising 0.5 to 10 parts by weight of the emulsifier.

8. A composition according to claim 7, comprising 0.6 to 4 parts by weight of the emulsifier.

9. A composition according to claim 1, wherein the emulsifier is an alkyl polyglycoside having a lipophilic group of $C_8$ to $C_{16}$ chain length.

10. A composition according to claim 1, wherein the oil phase comprises at least 30% by weight, based on the oil phase weight, of a dialkyl ether.

11. A composition according to claim 10, wherein the oil phase comprises at least 50% by weight, based on the oil phase weight, of a dialkyl ether.

12. A composition according to claim 1, wherein the co-emulsifier is selected from the group consisting of fatty acid polyol partial esters, fatty alcohols, and fatty alcohol polyol ethers.

13. A composition according to claim 1, wherein the weight ratio of emulsifier to co-emulsifier is 1:1 to 20:1.

14. A composition according to claim 13, wherein the weight ratio of emulsifier to co-emulsifier is 2:1 to 15:1.

15. A translucent antiperspirant composition in the form of a sprayable fine-droplet oil-in-water emulsion, consisting essentially of:
   a) 0.5% to 30% by weight of a dermatologically compatible water-immiscible oil phase comprising at least 50% by weight of a di-n-alkyl ether;
   b) 40% to 90% by weight of water;
   c) 0.35 to 30 parts by weight per part by weight of oil phase of a hydrophilic nonionic emulsifier of the formula:

   RO—(Z)$_x$ wherein R is $C_8$ to $C_{22}$ alkyl or alkenyl, Z is a monosaccharide, and x is the degree of oligomerization being a number of 1.1 to 1.5; and
   d) 0.1% to 25% by weight of an inorganic astringent antiperspiration agent selected from the group consisting of aluminum, zirconium, and zinc salts,
   wherein the size of the droplets is essentially between 10 nm and 100 nm.

16. A translucent microemulsion concentrate comprising:
   a) 20% to 40% by weight of water;
   b) 20% to 40% by weight of a dermatologically compatible water-insoluble oil phase; and
   c) 0.35 to 30 parts by weight per part by weight of the oil phase of a hydrophilic nonionic emulsifier,
   wherein the microemulsion concentrate comprises an oil phase dispersed as droplets in a continuous aqueous phase, said droplets having a size of essentially 1 to 100 nm.

17. A microemulsion concentrate according to claim 16, wherein the hydrophilic nonionic emulsifier is an alkyl polyglycoside of the formula:

RO—(Z$_x$)

wherein R is $C_8$ to $C_{22}$ alkyl or alkenyl, Z is a monosaccharide, and x is the degree of oligomerization being a number of 1.1 to 1.5.

18. A microemulsion concentrate according to claim 16, further comprising 0.1% to 10% by weight of a perfume oil.

19. A process for preparing the microemulsion concentrate of claim 16, comprising the steps of dissolving all water-soluble components in the water to form an aqueous phase, dissolving all oil-soluble components in the oil phase, and intensively mixing the aqueous and oil phases at 10° C. to 90° C. to form the microemulsion concentrate of claim 16.

20. A process for the production of a translucent antiperspirant composition comprising the step of intensively mixing the microemulsion concentrate of claim 16 with an aqueous solution of an antiperspiration agent.

21. A translucent antiperspirant composition in the form of a sprayable, fine-droplet, oil-in-water emulsion, obtained mixing 0.5% to 30% by weight of a water-immiscible dermatologically compatible oil phase, 40% to 90% by weight of water, 0.35 to 30 parts by weight of a hydrophilic nonionic emulsifier per part by weight of the oil phase, and 0.1% to 25% by weight of an inorganic astringent antiperspiration agent to form said emulsion, wherein the size of the droplets is essentially between 10 nm and 100 nm, said weight percents being based on the weight of the emulsion.

22. A translucent antiperspirant composition in the form of a sprayable fine-droplet oil-in-water emulsion obtained by mixing 0.5% to 30% by weight of a dermatologically compatible water-immiscible oil phase comprising at least 50% by weight of a di-n-alkyl ether, 40% to 90% by weight of water, 0.35 to 30 parts by weight per part by weight of oil phase of a hydrophilic nonionic emulsifier of the formula:

RO—(Z)$_x$ wherein R is $C_8$ to $C_{22}$ alkyl or alkenyl, Z is a monosaccharide, and x is the degree of oligomerization being a number of 1.1 to 1.5, and 0.1% to 25% by weight of an inorganic astringent antiperspiration agent selected from the group consisting of aluminum, zirconium, and zinc salts to form said emulsion, wherein the size of the droplets is essentially between 10 nm and 100 nm.

23. A translucent microemulsion concentrate obtained by mixing 20% to 40% by weight of water, 20% to 40% by weight of a dermatologically compatible water-insoluble oil phase, and 0.35 to 30 parts by weight per part by weight of the oil phase of a hydrophilic nonionic emulsifier to disperse said oil phase as droplets in said aqueous phase, said droplets having a size of essentially 1 to 100 nm, and said weight percents being based on the weight of said microemulsion concentrate.

* * * * *